US00PP25685P2

(12) United States Plant Patent
Davey et al.

(10) Patent No.: US PP25,685 P2
(45) Date of Patent: Jul. 7, 2015

(54) ***HELLEBORUS* PLANT NAMED 'EPBRD01'**

(50) Latin Name: *Helleborus×hybridus*
Varietal Denomination: EPBRD01

(71) Applicants: Rodney Davey, Axminster (GB); Lynda Windsor, Axminster (GB)

(72) Inventors: Rodney Davey, Axminster (GB); Lynda Windsor, Axminster (GB)

( * ) Notice: Subject to any disclaimer, the term of this patent is extended or adjusted under 35 U.S.C. 154(b) by 155 days.

(21) Appl. No.: 13/986,832

(22) Filed: Jun. 10, 2013

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'EPBRD01', characterized by its upright and mounding plant habit; uniform and freely flowering habit; greenish white-colored flowers held above the foliar plane on relatively long peduncles; and good garden performance.

2 Drawing Sheets

Botanical designation: *Helleborus×hybridus.*
Cultivar denomination: 'EPBRD01'.

BACKGROUND OF THE INVENTION

The present invention relates to a new and distinct cultivar of *Helleborus* plant, botanically known as *Helleborus×hybridus* and hereinafter referred to by the name 'EPBRD01'.

The new *Helleborus* plant is a product of a planned breeding program conducted by the Inventors in Devon, United Kingdom. The objective of the breeding program was to create new freely-flowering *Helleborus* plants with long peduncles that hold the flowers above the foliar plane and good flower longevity.

The new *Helleborus* plant originated from a cross-pollination conducted by the Inventors in Devon, United Kingdom in February, 2008 of a proprietary seedling selection of *Helleborus×hybridus* identified as code number 731-RDMX, as the female, or seed, parent, not patented, with a proprietary seedling selection of *Helleborus×hybridus* identified as code number 3465RDMT47, as the male, or pollen, parent, not patented. The new *Helleborus* plant was discovered and selected by the Inventors as a single flowering plant from within the progeny of the stated cross-pollination grown in a controlled greenhouse environment in Devon, United Kingdom in January, 2010.

Asexual reproduction of the new *Helleborus* plant by tissue culture in a controlled greenhouse environments in Aalsmeer and Boijl, The Netherlands since April, 2010, has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'EPBRD01'.

These characteristics in combination distinguish 'EPBRD01' as a new and distinct *Helleborus* plant:

1. Upright and mounding plant habit.
2. Uniform and freely flowering habit.
3. Greenish white-colored flowers held above the foliar plane on relatively long peduncles.
4. Good garden performance.

Compared to plants of the female parent selection, plants of the new *Helleborus* are more freely flowering. Compared to plants of the male parent selection, plants of the new *Helleborus* hold their flowers higher above the foliar plane.

Plants of the new *Helleborus* can be compared to plants of *Helleborus×hybridus* 'ABCRD01', disclosed in U.S. Plant Pat. No. 24,149. In side-by-side comparisons conducted in Devon, United Kingdom, plants of the new *Helleborus* differed from plants of 'ABCRD01' in the following characteristics:

1. Plants of the new *Helleborus* had larger leaves than plants of 'ABCRD01'.
2. Plants of the new *Helleborus* were more freely flowering than plants of 'ABCRD01'.
3. Plants of the new *Helleborus* had larger flowers than plants of 'ABCRD01'.
4. Plants of the new *Helleborus* and 'ABCRD01' differed in flower color as plants of 'ABCRD01' had red purple-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'EPBRD01' grown in a container.

The photograph on the second sheet is a close-up view of a typical flower of 'EPBRD01'.

DETAILED BOTANICAL DESCRIPTION

The aforementioned photographs and following observations, measurements and values describe plants grown during the winter in three-liter containers in an outdoor nursery in Boijl, The Netherlands and under cultural practices typical of commercial *Helleborus* production. During the production of the plants, day temperatures ranged from 0° C. to 10° C. and night temperatures ranged from −15° C. to 0° C. Plants were one year old when the photographs and the description were taken. In the following description, color references are made to The Royal Horticultural Society Colour Chart, 2001 Edition, except where general terms of ordinary dictionary significance are used.

Botanical classification: *Helleborus hybridus* 'EPBRD01'.

Parentage:

*Female, or seed, parent.*—Proprietary seedling selection of *Helleborus×hybridus* identified as code number 731-RDMX, not patented.

*Male, or pollen, parent.*—Proprietary seedling selection of *Helleborus×hybridus* identified as code number 3465RDMT47, not patented.

Propagation:

*Type.*—By tissue culture.

*Time to initiate roots, summer.*—About four weeks at 20° C.

*Time to produce a rooted young plant, summer.*—About two months at 20° C.

*Root description.*—Fleshy; white to brown in color.

*Rooting habit.*—Vigorous.

Plant description:

*Plant and growth habit.*—Herbaceous perennial; upright and mounding plant habit with flowers held above the foliar plane; moderately vigorous to vigorous growth habit.

*Plant height.*—About 23 cm to 35 cm.

*Plant diameter* (*area of spread*).—About 20 cm to 25 cm.

Leaf description:

*Arrangement.*—Leaves arranged alternately in a basal rosette; leaves palmately compound with three to five leaflets per leaf.

*Leaflet length.*—About 10 cm to 12 cm.

*Leaflet width.*—About 8 cm to 10 cm.

*Leaflet shape.*—Palmate; elliptic to ovate.

*Leaflet apex.*—Acute.

*Leaflet base.*—Cordate to acute.

*Leaflet margin.*—Dentate to serrate.

*Leaflet texture, upper and lower surfaces.*—Smooth, glabrous; leathery.

*Leaflet venation pattern.*—Pinnate.

*Leaflet color.*—Developing and fully expanded leaves, upper surface: Close to 139A; venation, close to 139C, at the base of the leaflet, close to 187A. Developing and fully expanded leaves, lower surface: Close to 138A; venation, close to 139C, at the base of the leaflet, close to 187A.

*Petioles.*—Length: About 16 cm. Diameter: About 5 mm. Texture, upper and lower surfaces: Smooth, glabrous. Color, upper and lower surfaces: Close to 166A.

Flower description:

*Flower shape and habit.*—Single-type rotate flowers arranged in loosely branched cymes; freely flowering habit with typically about two to four per cyme and up to 60 flowers developing per plant in the second year of growth; flowers facing outwardly and nodding.

*Fragrance.*—None detected.

*Natural flowering season.*—Plants begin flowering about two months after planting; plants flower from January until March in the United Kingdom.

*Flower longevity on the plant.*—About two months; flowers persistent.

*Inflorescence height.*—About 25 cm to 30 cm.

*Inflorescence diameter.*—About 15 cm to 20 cm.

*Flower buds.*—Length: About 2 cm to 3 cm. Diameter: About 1 cm to 2 cm. Shape: Elliptic to ovate. Color: Close to 193A.

*Flower diameter.*—About 8 cm.

*Flower depth* (*height*).—About 2 cm.

*Petals.*—None observed; transformed into nectaries.

*Sepals.*—Quantity and arrangement: Five arranged in a single whorl. Length: About 4 cm. Width: About 3 cm to 4 cm. Shape: Elliptic to obovate. Apex: Rounded to obtuse. Base: Cuneate. Margin: Entire. Texture, upper and lower surfaces: Smooth, glabrous. Color: When opening and fully opened, upper surface: Close to 157D; towards the base, close to 142B. When opening and fully opened, lower surface: Close to 157D.

*Peduncles.*—Length: About 20 cm. Diameter: About 5 mm. Strength: Strong. Aspect: Mostly upright to outwardly slanting. Texture: Smooth, glabrous. Color: Close to 166A.

*Pedicels.*—Length: About 4 cm. Diameter: About 2 mm. Aspect: About 10° from peduncle axis. Strength: Strong. Texture: Smooth, glabrous. Color: Close to 142A.

*Reproductive organs.*—Stamens: Quantity per flower: About 60. Filament length: About 1.5 cm. Filament color: Close to 157D. Anther shape: Elliptic to ovate. Anther length: About 2 mm. Anther color: Close to 10B. Pollen amount: Scarce. Pollen color: Close to 10B. Pistils: Quantity per flower: About five. Pistil length: About 2.5 cm. Stigma shape: Club-shaped. Stigma color: Close to 157C. Style length: About 1.5 cm. Style color: Close to 183D. Ovary color: Close to 142B.

*Nectaries.*—Quantity per flower: About 10 to 14. Length: About 5 mm to 7 mm. Width: About 2 mm to 3 mm. Shape: Funnelform. Color: Close to N144B; towards the apex, close to 149B.

*Seeds and fruits.*—Seed and fruit development have not been observed on plants of the new *Helleborus*.

Garden performance: Plants of the new *Helleborus* have been observed to have good garden performance and to tolerate rain, wind and temperatures ranging from about −20° C. to about 35° C.

Pathogen & pest resistance: Plants of the new *Helleborus* have not been observed to be resistant to pathogens and pests common to *Helleborus* plants.

It is claimed:

1. A new and distinct *Helleborus* plant named 'EPBRD01' as illustrated and described.

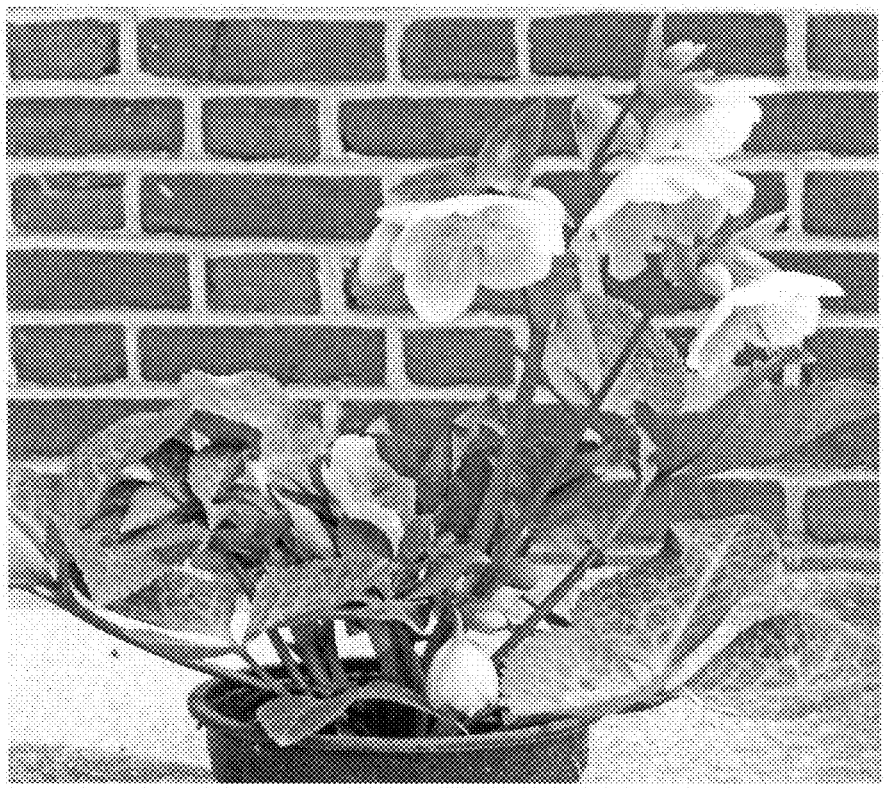

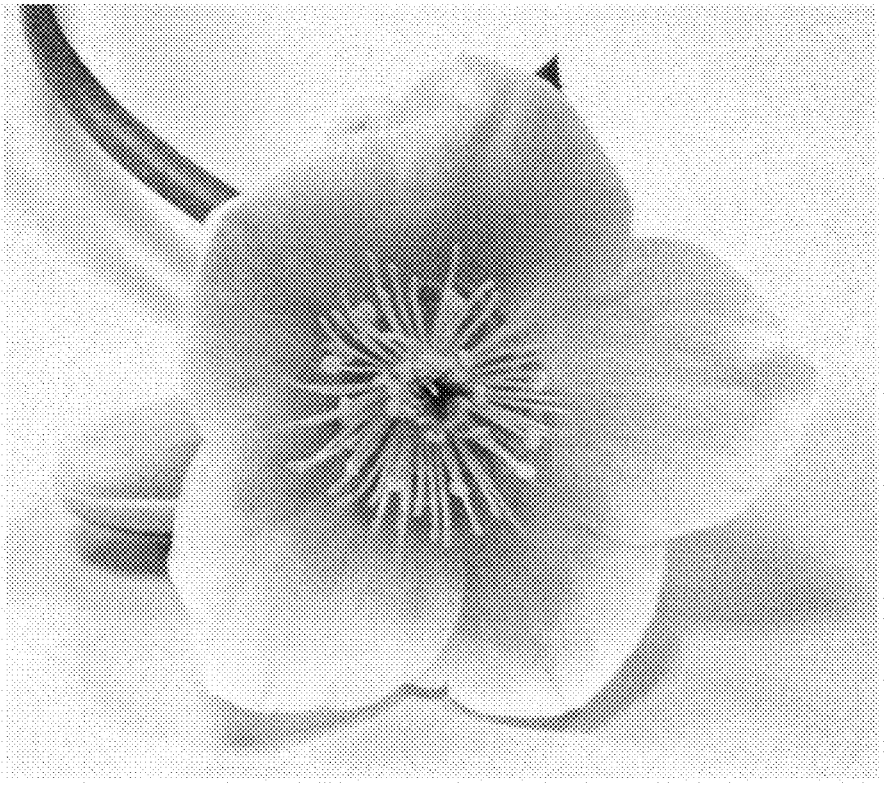

* * * * *